(12) United States Patent
Van Rijn et al.

(10) Patent No.: US 6,369,036 B1
(45) Date of Patent: *Apr. 9, 2002

(54) ANTIFUNGAL COMPOSITION (75) Inventors: Ferdinand Theodorus Van Rijn, Delft; Jacobus Stark, Rotterdam; Hong Sheng Tan, Bleiswijk; Willem Johan Van Zoest, Schiedam; Nicolaas Cornelis Barendse, Den Hoorn, all of (NL)

(73) Assignee: DSM N.V. (NL)

(*) Notice: Subject to any disclaimer, the term of this patent is extended or adjusted under 35 U.S.C. 154(b) by 0 days.

This patent is subject to a terminal disclaimer.

(21) Appl. No.: 09/069,534

(22) Filed: Apr. 30, 1998

Related U.S. Application Data (63) Continuation of application No. 08/446,782, filed as application No. PCT/EP94/03245 on Sep. 28, 1994, now Pat. No. 5,821,233.

(30) Foreign Application Priority Data

Sep. 29, 1993 (EP) .............................................. 93202791

(51) Int. Cl.$^7$ .......................... A61K 31/70; C07H 17/08
(52) U.S. Cl. .......................... 514/31; 536/6.5; 536/18.5
(58) Field of Search ................................ 536/6.5, 18.5; 514/31

(56) References Cited

U.S. PATENT DOCUMENTS

| | | | | |
|---|---|---|---|---|
| 3,892,850 A | * | 7/1975 | Struyk et al. | ................ 424/119 |
| 4,148,891 A | * | 4/1979 | Smink | ......................... 514/31 |
| 4,600,706 A | | 7/1986 | Carter | |
| 4,812,312 A | | 3/1989 | Lopez-Berenstein et al. | |
| 5,821,233 A | * | 10/1998 | Van Rijn et al. | .............. 514/31 |

OTHER PUBLICATIONS

Jedrychowski, L.; Reps, A.; Jarmul, I.; Babuchowski, A. "Use of natamycin for a protection of semihard cheeses against moulding" Brief communications of the XXIII International Dairy Congress, Montreal, Oct. 8–12, 1990, vol. I.
Daamen, C.B.G. and Berg, G. van den; "Prevention of mould growth on cheese by means of natamycin", Voedingsmiddelentechnologie, 18 (2) 26–29 (1985).
Neviani, E.; Emaldi, G.C.; Carini S, "Use of pimaricin as a fungicide on cheese rind: technology and the effects on the cheese surface flora".
Morris, H.A.;. Castberg, H.B.; "Control of Surface Growth on Blue Cheese Using Pimaricin" Cultured Diary Products Journal, 15 (2), 21–23 (1980).
Baldini, P.; Palmia, F; Raczynski, R.G.; Campanini, M. "Use of pimaricin for preventing mould growth on Italian cured meat products" Industria Conserve, 54 (4), 305–307, (1979).
Weiss, G; "Preservation of dairy products with chemicals" Deutsche Molkerei Zeitung 91 (50), 2351–2356, (1970).
Holley, R.A.; "Effect of Sorbate and Pimaricin on Surface Mold and Ripening of Italian Dry Salami" Lebensmittel Wissenschaft und Technologie 19 (1), 59–64, (1986).
Ruig, W.G; Berg, G. van den; "Influence of the fungicides sorbate and natamycin in cheese coatings on the quality of the cheese" Netherlands Milk and Dairy Journal, 39 (3), 165–172, (1985).
Holley, R.A.; "Prevention of Surface Mold Growth on Italian Dry Sausage by Natamycin and Potassium Sorbate" Applied and Environmental Microbiology, 41 (2), 422–429 (1981).
Lueck, H.; Cheesman, C.E.; "Mould growth on cheese as influenced by pimaricin (natamycin) or sorbate treatments" South African Journal of Dairy Technology, 10 (3), 143–146, (1978).
Mattson, N. "Mould control on cheese. Experience with potassium sorbate (added to brine) and pimaricin for surface treatment of hard cheese" Svenska Mejeritidningen 69 (3), 14–15, (1977).
Verma, H.S.; Yadav, J.S.; Neelakantan, S.; "Preservative effect of selected antifungal agents on butter and cheese" Asian Journal of Dairy Research 7, (1), 34–38, (1988).
Clark, W.L.; Shirk, R.J.; Kline, E.F.; "Pimaricin, a new fungistat" Microbial Inhibitors in Food, Edition N. Molin, 167–184 (1964).
Brik, H.; "Natamycin" Analytical Profiles of Drug Substances 10, 513561, (1981).
Ghielmetti, G.;Bruzzese, T.; Bianchi, C.; Recusani, F.; "Relationship between Acute Toxicity in Mice and Polymorphic Forms of Polyene Antibiotics " Journal of Pharmaceutical Sciences 65 (6), 905–907, (1976).

* cited by examiner

Primary Examiner—Elli Peselev
(74) Attorney, Agent, or Firm—Morrison & Foerster LLP (57) ABSTRACT

The present invention provides a method of preparing an improved antifungal composition containing an antifungal compound of the polyene type such as natamycin wherein the antifungal compound is incorporated into the composition in a form which shows an enhanced activity, e.g. in the form of a solution and/or being in a modified polymorphic form.

7 Claims, 6 Drawing Sheets

ANTIFUNGAL COMPOSITION

The present application is a continuation of Ser. No. 08/446,782, now U.S. Pat. No. 5,821,233, filed May 26, 1995 which is the U.S. national stage of International Application PCT/EP94/03245, itself internationally filed on Sep. 28, 1994, each of these applications being incorporated by reference herein as if fully set forth.

The present invention relates to the preparation of compositions which comprise an antifungal compound of the polyene type such as natamycin, and the use of such compositions to treat foodstuffs or agricultural products or for pharmaceutical purposes.

BACKGROUND OF THE INVENTION

For more than 20 years, natamycin has been used to prevent the growth of mould on cheese and sausages. (Ref. 1–12).

Cheeses are treated by immersion in a suspension of natamycin in water or by coating with a natamycin—containing aqueous emulsion of a polymer, commonly an aqueous emulsion of polyvinyl acetate. Sausages are mainly treated by immersion or by spray coating with a suspension of natamycin in water. Usually aqueous suspensions of natamycin for immersion treatments contain 0.1 to 0.2% w/v of natamycin, while polymer emulsions for coating purposes containing natamycin have a natamycin content of 0.01 to 0.05% w/v.

Mostly these treatments are highly effective in preventing spoilage by mould. However, because of the low solubility of natamycin, spoilage by some fungi which have relatively low susceptibility to natamycin may still occur due to lack of full inhibition.

The present invention relates to a process for improving the activity of polyene antifungal compounds, in particular natamycin, towards mould, and to compositions prepared according to said process. In particular, such compositions are useful for combatting yeasts and fungi which are normally relatively resistant to the action of antifungal compounds of the polyene type.

SUMMARY OF THE INVENTION

Unexpectedly, it has been found that the activity of antifungal compounds of the polyene type, such as natamycin, towards yeast and fungi can be markedly enhanced by one of the following methods.

(1) By modifying the polymorphic form. Firstly the polyene antifungal compound can be converted into a solvated form by contacting the compound with a solvent. An example of such a solvate is natamycin methanol solvate.

Secondly the solvated solvent molecules may be removed from the crystal lattice of the solvate. An example of such a compound is δ-natamycin, which can be obtained by subjecting natamycin methanol solvate to diminished pressure over phosphorous pentoxide.

Thirdly the "empty" room of the crystal lattice may be refilled with other solvent molecules; e.g. by contacting the "empty" compound with a solvent or the vapour thereof. Examples of such compounds are the solvates of natamycin with the following solvents; methanol, ethanol, n-propanol, n-butanol, methoxy-ethanol, dichloromethane, 1,2-dichloroethane, methyl formate, ethyl formate, acetonitrile, formamide, N-N-dimethyl formamide and dimethyl sulphoxide.

Finally new polymorphic forms of polyene antifungal compounds may be obtained by subjecting the compound with the "empty" crystal lattice to a humid condition. For example when δ-natamycin is subjected to 76% RH a new trihydrated crystal modification is obtained. This new compound, which is named γ-natamycin, has an enhanced activity towards species which are normally relatively resistant to the action of the original α-natamycin, which is also a trihydrated form of natamycin (see Ref. 14, p. 520).

(2) Prior to incorporating the antifungal compound into a food treatment composition or into a pharmaceutical preparation the antifungal compound is dissolved in a suitable solvent system.

Suitable solvent systems for dissolving the fungicide are lower alcohols, e.g. a lower alcohol having 1 to 4 carbon atoms, glacial acetic acid, aqueous acid and alkaline solutions, and appropriate mixtures thereof. Examples of suitable alcohols are methanol, ethanol, n-propanol, isopropanol, ethylene glycol, ethoxy ethanol, propylene glycol and glycerol. Examples of suitable acidic solutions are aqueous solutions of hydrochloric acid, citric acid and acetic acid. Examples of suitable aqueous alkaline solutions are aqueous solutions of ammonia, alkali metal hydroxides and ethanolamine.

(3) By preparing an earthalkaline salt. Examples are the barium and the calcium salt of natamycin.

(4) By applying on a carrier. An example is natamycin on fumed silica, which can be prepared by mixing a solution of natamycin in methanol with fumed silica and removing the solvent by evaporating at diminished pressure. Preparations and compositions according to the invention are characterized by a high release profile of the antifungal compound in comparison to the unmodified polyene when measured by the method described in Example 1.

Therefore the invention relates to a method of preparing an anti-fungal composition containing an anti-fungal compound of the polyene type characterised in that said anti-fungal compound is incorporated into the composition in a modified form which shows an enhanced release profile of said anti-fungal compound in comparison to the unmodified anti-fungal compound. The anti-fungal compound can be brought in the modified form for example by modifying the polymorphic form and/or bringing the compound in a suitable solution. By unmodified form is meant the form given in 'The Merck Index', an encyclopedia of chemicals, drugs and biologicals or by the production referred to in The Merck Index.

According to one aspect of the invention a novel natamycin form and/or compound is disclosed. This compound is preferably selected from the group consisting of Natamycin methanol solvate, stabilized by storing under nitrogen gas and/or at −30° C.;

δ-natamycin;

γ-natamycin;

Calcium salt of natamycin;

Barium salt of natamycin;

The solvates of natamycin with: ethanol: 1-propanol, 1-butanol, 2--methoxyethanol, methyl formate, ethyl formate, acetone, dichloromethane, acetonitrile dimethylformamide, dimethyl sulphoxide, and formamide; and Natamycin on fumed silica as a carrier.

These compounds all have an improved release of the antifungal compound compared to unmodified α-natamycin.

Thus the present invention also provides a method of assessing the efficacy of an anti-fungal composition for inhibition of fungal or yeast cell growth at a surface which comprises the steps of:

(i) applying a sample of the composition to a carrier;
(ii) applying the carrier thus loaded to the surface of an agar plate containing yeast or fungal cells such that the composition is in contact with the agar surface;
(iii) incubating the agar plate and carrier at a temperature such that growth of said cells is inhibited; and
(iv) removing the carrier from the agar plate;
(v) incubating the agar plate under growth permitting conditions for said cells; and
(vi) determining inhibition of cell growth in the agar due to the presence of fungicide released from the composition sample.

In particular, the method is suitable for determining the availability of active anti-fungal components from preparations meant for surface treatments. Further the method is especially suitable for the determination of the dissolution of active anti-fungal components which have a low solubility in water.

Preparations containing activated fungicide are useful for preventing the growth of fungi which are normally relatively resistant to the action of polyene fungicides. Examples of fungi which have relatively low susceptibility towards natamycin are *Verticillium cinnabarinum, Botrytis cinerea* and *Trichophyton* species. Among *Aspergillus, Fusarium* and *Penicillin* species, species exhibiting relatively high tolerance to natamycin may also be found. An example of such a species is *Penicillium echinulatum var. discolor.*

Thus, in one aspect the present invention provides methods of preparing an anti-fungal composition containing an anti-fungal compound of the polyene type which is activated by one of the above mentioned methods. In a further aspect, the invention also provides compositions thus prepared.

In yet another aspect, the invention provides a method of treating a food or agricultural product to inhibit yeast or fungal growth which comprises applying a composition of the invention.

In principle, a solution of an anti-fungal compound of the polyene type may be incorporated into all kinds of preparations which are suitable for treating foodstuffs such as cheese and sausages and/or for treating agricultural products such as fruit, vegetables and seed. Suitable preparations for treating foodstuffs such as cheese and sausages are, for instance, coating emulsions which can be applied by brushing or by using a spray device and liquid preparations which can be used for immersion treatments. Preferably the pH of a preparation according to the invention for food or agricultural product treatment is from 1 to 10, more preferably from 2 to 8 and most preferably from 3.5 to 7.5. Further, the invention concerns foods and agricultural products when so treated.

Finally, the activated fungicide of the polyene type may also be incorporated into pharmaceutical preparations, for instance for topical application. Examples of suitable pharmaceutical preparations are lotions, creams and ointments.

DETAILED DESCRIPTION OF THE INVENTION

The invention provides novel types of polyene anti-fungal preparations and compositions to prevent spoilage of foodstuffs and/or agricultural products by mould and for use as a pharmaceutical. The compositions are characterised by enhanced anti-fungal activity of the polyene fungicide towards species which normally exhibit relatively high tolerance towards such compounds. As mentioned above, examples of fungi which are relatively resistant towards natamycin are *Verticillium cinnabarinum, Botrytis cinerea* and *Trichophyton* species. Among *Aspergillus, Fusarium* and *Penicillium* species, species exhibiting relatively high tolerance to natamycin may also be found. An example of such a species is *Penicillium echinulatum var. discolor.*

The enhanced activity of a composition of the present invention is presumably due to improved availability of the anti-fungal compound, e.g. natamycin, as a result of improved dissolution. In general, only fungicide which is in solution will be available to exert anti-fungal activity. Thus, in the case of a fungicide with a low solubility the following these factors will have an influence on the final fungicidal effect: the dissolution of the fungicide, the diffusion of the dissolved fungicide to the site of infection and the elimination of the dissolved fungicide. Natamycin for instance may be deactivated by decomposition through the action of light or by hydrolysis. (Ref. 2). Natamycin has a MIC (minimal inhibitory concentration) of less than 10 ppm for most foodborn fungi, while its solubility in water is from 30 to 50 ppm (Ref. 13). In most cases, the efficacy of natamycin in conventional anti-fungal preparations towards such fungi will thus not be limited significantly by solubilisation or diffusion factors, because the solubility is far higher than the MIC value. Elimination of dissolved natamycin will be compensated sufficiently by dissolution of undissolved natamycin and by diffusion of dissolved natamycin to the site of infection.

In the case of fungi with relatively low susceptibility to polyene fungicides, for example *Penicillium echinulatum var. discolor* solubilisation and diffusion of such a fungicide may however have a more limiting effect on its inhibitory activity. When a conventional fungicide preparation containing natamycin is employed, at the state of equilibrium the average dissolved portion of natamycin may drop beneath the effective concentration because elimination will not be adequately compensated by dissolution and diffusion of the anti-fungal compound. Usually this kind of problem can be overcome by improving the solubility of the active agent by appropriate selection of solvents or by use of a smaller particle size to improve the rate of solubilisation and to compensate for the diffusion limitations by increasing the density of the particle distribution on the surface to be treated. However, these well-known measures do not have the desired effect when applied to natamycin in aqueous suspension.

When natamycin is applied in a solvent such as glycerol to the surface of for instance cheese which is inoculated with *Penicillium echinulatum var. discolor*, it does not adequately suppress the growth of the fungus. Also, the use of a micronised sample gives little improvement in result as compared to the use of a non-micronised sample.

In the first case, probably the concentration of active natamycin on the surface of the cheese falls too low to effectively suppress the growth of the fungus as a result of too rapid diffusion of the dissolved natamycin into the cheese. In the second case, improvement of the solubilisation rate is not sufficient to give the desired improvement in anti-fungal activity.

Surprisingly, it has now been found that when natamycin is first dissolved in a solvent and then incorporated into an aqueous composition which may contain a second composition component, the activity of the fungicide towards fungal species with a low susceptibility to natamycin is markedly improved.

Thus, compositions according to the invention are prepared by dissolving an antifungal compound of the polyene type in a suitable solvent system prior to incorporation of the compound in a preparation suitable for application to a foodstuff or agricultural product or prior to combining the compound with a pharmaceutical excipient to provide a pharmaceutical composition, e.g. for topical use.

Suitable solvent systems are lower alcohols such as methanol, ethanol, propanol, ethylene, glycol, propylene glycol and glycerol and mixtures thereof.

Further, in a suitable alcoholic solvent, one or more hydroxyl groups may be linked by an ester bond to a fatty acid or linked to another alcohol group by an ether bond. Examples of such solvents are methoxy ethanol and ethoxy ethanol.

Suitable solvent systems are also glacial acetic acid and aqueous acid and alkaline solutions and mixtures of such solvents with the alcoholic solvents mentioned above. Examples of suitable aqueous acid and alkaline solutions include aqueous solutions of hydrochloric acid and citric acid and aqueous solutions of alkali metal hydroxides. Further solubilisers such as surfactants may be of advantage in dissolving the polyene fungicide into the solvent system. Examples of suitable solubilizers are sodium lauryl sulphate, dioctyl sulphosuccinate, calcium chloride, or surfactants of the non-ionic type, for instance those which are known under the brand names Tween, Span, Brij and Myrj.

The solution of the antifungal compound may be incorporated into the final composition by adding the solution to a preparation of vice versa. In principle, the solution of the antifungal compound may be incorporated into any kind of composition known to be suitable for treating a foodstuff and/or an agricultural product or for pharmaceutical purposes.

Compositions according to the invention have a characteristic fungicide release profile when measured according to the method described in Example 1. The method described in that example to measure the release of a fungicide, e.g. natamycin, from an anti-fungal composition is also a feature of the invention. In this method, a sample of the anti-fungal composition to be tested is applied to a carrier, e.g. a filter paper disc, and the fungicide is then permitted to migrate from the composition sample into agar loaded with a yeast or fungus over a certain time period and at a temperature at which cell growth is inhibited. A practical period is for instance 24 hours. However other time periods may also be chosen. After transferring the carrier to a fresh agar plate, the fungicide released from the carrier into the agar in the first agar plate can be determined by known microbiological methods, e.g. by incubation at 30° C. for 24 hours and measuring the inhibition zone. By repeating the procedure, the availability of the fungicide for inhibition of yeast or fungus growth can be measured until no more fungicide is released from the carrier.

Thus, in a still further aspect, the present invention provides a method of assessing the efficacy of an anti-fungal composition for inhibition of fungal or yeast cell growth at a surface which comprises the steps of:

(i) applying a sample of the composition to a carrier;

(ii) applying the carrier thus loaded to the surface of an agar plate containing yeast or fungal cells such that the composition is in contact with the agar surface;

(iii) incubating the agar plate and carrier at a temperature such that growth of said cells is inhibited; and (iv) removing the carrier from the agar plate;

(v) incubating the agar plate under growth permitting conditions for said cells; and (vi) determining inhibition of cell growth in the agar due to the presence of fungicide released from the composition sample.

Preferably a carrier is employed which can be regularly transferred from one agar plate to another plate. Preferably, the carrier should withstand at least 10 to 15 daily transfers without disturbing the microbiological measurements.

In particular, the method is particularly suitable for determining the availability of active anti-fungal components from preparations meant for surface treatments. Further the method is especially suitable for the determination of the dissolution of active anti-fungal components which have a low solubility in water.

Under the test conditions of the method of Example 1, a suspension of natamycin in water or in a polyvinyl acetate emulsion normally has an initial natamycin release rate of about 1 to 2 $\mu$g/day. Under the same conditions, compositions according to the invention exhibit a fungicide release rate of at least about 3 $\mu$g/day over at least the first day. A fungicide release rate as high as about 20 $\mu$g/day or even higher may be observed.

Further it was unexpectedly found that by modifying the polymorphic form the activity of polyene antifungal compounds towards less susceptible species can also be enhance. For instance when measured according to the method of Example 1 it could be shown that the methanol solvate of natamycin has an improved dissolution profile in comparison to that of the original well known natamycin trihydrate. (The well known natamycin trihydrate like described in e.g. ref. 14 will be further referred to as α-natamycin.)

Polymorphic forms of some polyene antifungal compounds are known. Ref. 15 for instance mentioned that the discrepancies of the acute toxicity values between various batches of polyene antifungal compounds, in particular of mepartricin and nystatin, could be attributed to polymorphic forms. At the other hand no differences of the microbiological activity between the different polymorphic forms of mepartricin or of nystatin were observed.

Ref. 14 (page 538) mentioned that the large discrepancies between the data of the solubility of natamycin from different literature sources could be attributed to the formation of solvates. The difference between the initial solubility of natamycin in methanol and the natamycin which remained in solution after the spontaneous crystallization was used as an illustration. This phenomenon was accounted to the formation of the (in methanol) less soluble methanol solvate. Upon contact with water however the crystals were rapidly converted back to the original form with the same X-ray diffraction pattern as the crystals isolated from aqueous solvents (page 519). Because of the rapid conversion of the methanol solvate to the original trihydrate upon contact with water the enhancement of the activity of natamycin methanol solvate under aqueous conditions towards species with a low susceptibility was very unexpected.

Further natamycin methanol solvate is an unstable substance (ref. 14, page 542) and therefore not very appropriate for practical use. Thus also a feature of the invention is the discovery that the substance can be stored for at least three months without decomposition when kept under inert gas and/or refrigerated conditions, e.g. under nitrogen and/or at −30° C. by Differential Scanning Calorimetric (DSC) measurements. Thermogravimetric and Differential Thermal Analysis (TG/DTA) and Nuclear Magnetic Resonance (NMR) analysis it could be shown that natamycin methanol solvate contains about 2 moles of methanol and about 0.5 mole of water per mole of natamycin.

As indicated by thermal analysis natamycin methanol solvate looses its methanol completely when subjected to diminished pressure over phosphorous pentoxide. X-ray analysis revealed that the result is a new crystal modification of natamycin, which will be further referred to as δ-natamycin. δ-Natamycin can be stored in a closed bottle without decomposition for more than 3 months, although the colour of the white substance tends to turn to yellow. Under refrigeration and/or inert conditions however, the substance can be kept for more than three months without discoloration. This is surprisingly because natamycin trihydrate which is extremely dried be subjecting to vacuo over phosphorus pentoxide when stored in a closed bottle looses 15% of its activity within 48 hours (Ref. 14, page 542).

Surprisingly δ-natamycin also has an improved dissolution and moreover also an enhanced activity towards species with a low susceptibility to natamycin.

Thus the invention also comprises substances which are obtained by removing (part of) the solvated solvent molecules from the crystal lattice of solvated polyene antifungal compounds, e.g. by subjection to diminished pressure over a water binding agent like phosphorous pentoxide or by the application of diminished pressure in combination with a small flow of an inert gas like nitrogen.

δ-Natamycin when stored at 76& RH is converted to a crystal modification which contain 3 moles of water per mole of natamycin. However as shown by X-ray analysis the new crystal form is different from the original α-modification.

Up till now polymorphism of natamycin thrihydrate is not known (Ref. 14, page 518). Thus this modification, which will be referred to as γ-natamycin, is a new compound. γ-Natamycin is a white stable substance which colour changes slowly to yellow when stored at ambient conditions. However when stored under inert gas conditions, e.g. under nitrogen, the colour remains white.

Furthermore as indicated by the improved dissolution γnatamycin also has an enhanced activity towards species with a low susceptibility in comparison to the α-modification.

Further δ-natamycin can be converted into a variety of solvates when subjected to the influence of vapours of several solvents. Thus also a feature of the invention are substances which are obtained by subjecting the "empty" crystal modification of the polyene antifungal compound with vapours of solvents.

Finally polymorphic forms of polyene antifungal compounds like natamycin can be obtained by contacting the α-, or δ- or γ-modification with solvent. Suitable solvents to prepare the polymorphic forms are those belonging to the groups of lower (polyhydric) alcohols, aliphatic ketones, halogenated aliphatic hydrocarbons, aliphatic cyano hydrocarbons, aliphatic ethers and aliphatic esters or mixtures thereof. Examples of suitable solvents are methanol, ethanol, methoxy ethanol, chloroform, methylene chloride, acetonitrile, dioxane, acetone and ethyl acetate. A small amount of moisture in the solvent system of up to 1% may also be present.

Another feature of the invention is the unexpected discovery that the activity of polyene antifungal compounds can also be enhanced by converting the compound into an earth alkaline metal salt.

Although metal complexes and sodium salts of polyene antifungal compounds are known and claimed for their improved activity up till now the earth alkaline salts are not known. Moreover the improvement of the activity of said compounds is mainly based on the improvement of the solubility of the substances in aqueous systems, while the enhanced activity of the salts according to the present invention towards species with a low susceptibility is due to the improved dissolution of the earth alkaline salts, in particular of the calcium and of the barium salt. U.S. Pat. No. 3957754 describes the preparation of complexes of polyene antibiotics with polyvalent cations. Complexes with trivalent cations are preferred because of their stability and of their good water-solubility.

U.S. Pat. No. 3476856 describes the preparation of the sodium salts of nystatin and other polyene antibiotics. The sodium salts are water-soluble.

Finally U.S. Pat. No. 3740424 describes the preparation of polyene macrolide antibiotic—borate complexes, which have an improved water solubility.

A last feature of the invention is the discovery that the activity of polyene antifungal compounds can also be improved by applying the compound on a carrier. Suitable carriers are fumed silica; micro crystalline cellulose powders like those of the Avicel® types and powders which are used as a filteraid. The polyene may be applied on the carrier by methods known perse; e.g., by spray coating technics of a solution of the antifungal on a carrier or by evaporating the solvent from a mixture of a solution of the antifungal and the carrier. Suitable solvents are methanol, ethanol, methoxy ethanol, ethoxy ethanol, chloroform and mixtures thereof.

The samples are characterized by the improved dissolution of the polyene antifungal compound when measured according to the method of Example 1.

Compositions according to the invention which may be used for the treatment of foodstuffs such as cheese or sausages may be, for example, liquids for treatment by immersion and/or by spraying, or coating emulsions like that of the polyvinyl acetate type or of the oil in water (o/w) or water in oil (w/o) type.

Compositions of the invention for the treatment of agricultural products such as flower bulbs, (kernel) grain and vegetables may be, for example, aqueous systems which may be used by methods known per se, e.g. dipping or spraying.

Examples of pharmaceutical compositions for topical application in which a solution of a polyene fungicide may be incorporated are lotions, creams and ointments.

The polyene antifungal agent may be natamycin, lucensomycin, nystatin or amphotericin B. Preferred polyenes are natamycin and lucensomycin.

The amount of fungicide, e.g. natamycin, in a liquid composition for immersion treatment may be from 0.01% to 2% w/v. Preferably, the amount is from 0.01% to 1% w/v. In principle, the imnmersion liquid may be of any kind. When an aqueous system is used, the addition of a surfactant may be of advantage, in particular for treating objects with a hydrophobic surface.

In a coating emulsion according to the invention, the amount of fungicide, e.g. natamycin, may be from 0.005% to 2% w/v, preferably from 0.01% to 1% w/v and more preferably from 0.01% to 0.5% w/v. The coating emulsion may be of the o/w or w/o type. Particularly preferred are emulsions prepared from coating emulsions commonly employed in the food industry. For example, for the treatment of hard cheese an aqueous polymer emulsion of the polyvinyl acetate type may be used.

As mentioned above, preferably the pH of a composition according to the invention for food or agricultural product treatment is from 1 to 10, more preferably from 2 to 8 and most preferably from 3.5 to 7.5. The pH of such a composition may be adjusted by any method known in the art, e.g. by adding an acidic or a basic compound or by using a buffering system. Useful acids for this purpose are for example citric acid, lactic acid, hydrochloric acid, phosphoric acid, sulphuric acid and tartaric acid. Useful basic compounds which may be alternatively employed are for example, sodium hydroxide, potassium hydroxide, ammonia and calcium hydroxide. Useful buffering systems which may be employed in compositions of the invention are for instance those of the ph citrate types.

The invention is illustrated by me following examples:
DSC-and TG/DTA—measurements
General procedure DSC and TG/DTA measurements were carried out using the SSC 5200 system of Seiko provided with the DSC 120 and the TG/DTA 220 furnaces.

Standard procedures were used to obtain the desired data. A sealed (UF-shaped) pan (A1) was chosen with a hole in the cover was used as a sample container. The hole in the cover was reproducibly made by using a standard needle.

| DSC | |
|---|---|
| temperature programme | −35 to 270° C. |
| heating rate | 5° C./min |
| sampling | 0.5 sec |
| atmosphere | nitrogen (80 ml/min) |
| reference | 1.154 mg of alumina in sealed pan (Al) with a hole in the cover |
| sample size | 1.20 ± 0.15 mg |
| sample container | 1.5 µl sealed sample container (Al) with a hole in the cover |
| TG/DTA | |
| temperature programme | 22 to 230° C. |
| heating rate | 2.5° C./min |
| sampling | 0.5 sec |
| atmosphere | nitrogen (100 ml/min) |
| reference | empty, open Pt pan |
| sample size | ±5 mg |
| sample container | open Pt pan |

X-ray analysis

The X-ray pattern of the different natamycin crystals were determined with a Guinier camera with a monochromator, type Johansson, utilizing CuKα radiation.

EXAMPLE 1

This example describes a microbiological method for determining the availability of an anti-fungal component from an anti-fungal composition. In this example, natamycin is the active component.

Filter paper disc (S&S Antibiotics Test Disc no. 321260) with a diameter of 0.6 cm were loaded with the preparation to be tested such that each disc was loaded with 40 µg of natamycin, e.g. 50 µl of a sample containing 800 ppm of natamycin was applied to a disc. The discs were then put on agar which was seeded with *Saccharomyces cerevisiae* ATCC 9763. The petri dishes containing the agar were then stored for 24 hours at 6° C. to permit the natamycin to release into the agar. Under these conditions, *Saccharomyces* does not grow. As a reference, discs were freshly loaded with a range of known amounts of natamycin dissolved in aqueous methanol.

The next day, the sample discs were transferred to new petri dishes containing agar seeded with *Saccharomyces cerevisiae*. New disc freshly loaded with a range of known quantities of dissolved natamycin were prepared for use as a reference. The new dishes with the sample discs and the new references were stored at 6° C. for 24 hours and the old dishes containing the released natamycin incubated at 30° C. for 24 hours.

The size of the inhibition zone is a measure of the natamycin released from the sample disc. The amount of released natamycin can be calculated by methods know per se. By repeating the procedure, the released natamycin can be measured on a daily basis. Other release time periods may alternatively be chosen.

EXAMPLE 2

Purification of α-natamycin

Under stirring 11 g of industrial grade natamycin was suspended in a mixture of 640 ml of water and 160 ml of n-propanol. The pH was adjusted to 9.9 by adding concentrated ammonia. The obtained solution was then treated with 11 g of carbon black and filtered over a Seitz filter. By adjusting the pH of the filtrate to 6.5 by means of a 50% solution of acetic acid the natamycin was brought to crystallisation.

The crystals were collected by filtration and washed with water. The crystalline mass was resuspended in 400 ml of water, filtered off and successively washed with 50 ml of water and 50 ml of acetone. After drying overnight at 40° C. in a ventilation box 7.78 g of natamycin was obtained. The material was equilibrated at 76% relative humidity to yield 7.83 g of α-natamycin.

The specific DSC data are: endotherms at $T_{top}$ 45.2, 65.9 and 104.7° C. (water) and an endotherm immediately followed by an exotherm at $T_{top}$ 205.6 and 221.2° C. respectively (decomposition).

The crystallographic data of the obtained material, which has now been defined as α-natamycin, are presented in table I. The data are in agreement with previous obtained data (Ref. 14, page 520)

EXAMPLE 3

Preparation of the methanol solvate of natamycin

Under stirring 25 g of purified α-natamycin was suspended in 2.5 l of methanol and heated to reflux. After 15 minutes the heating mantle was removed and the suspension was stirred overnight. The crystals were filtered off and washed with 500 ml of methanol.

The crystalline material was then dried in vacuo for 1 hour at room temperature to yield 21.9 g of natamycin methanol solvate.

The presence of methanol was proved by NMR analysis. The DSC thermogram showed two endotherms at $T_{top}$ 53.4 and 71.5° C. (methanol), an endotherm at $T_{top}$ at 123.5° C. (water) and an endotherm immediately followed by an exotherm at $T_{top}$ 181.2 and 186.1° C. respectively (decomposition).

The preparation of the methanol solvate can also be performed at room temperature without previous heating and at a higher concentration, e.g. 100 g of natamycin in 1 l of methanol. In this case no clear solution will be obtained prior to the formation of the methanol solvate. Usually the conversion of the α-natamycin to the methanol solvate is completed within 15 minutes.

The crystallographic data of the obtained natamycin methanol solvate are presented in table I.

Stability of Natamycin Methanol Solvate

Samples of 100 mg of natamycin methanol solvate were stored at respectively 20° C., and 31 35° C. in an air or in a nitrogen atmosphere.

The decomposition rate of natamycin methanol solvate was decreased considerably by storing under nitrogen and/or at low temperature.

After two days storage of the methanol solvate at room temperature in air atmosphere no discoloration was observed. According to DSC analysis the material was still intact. After 5 days storage a slightly yellow coloured product was obtained, which was decomposed rather seriously. At 4° C. the methanol solvate was still intact after 12 days storage, but after 19 days strong decomposition was detected.

When stored under refrigeration at −35° C. however even after three months the methanol solvate was still uncoloured and showed no evidence of decomposition. By storage under nitrogen atmosphere the stability of the methanol solvate was highly improved. Even after three months at room temperature no discoloration or decomposition was observed.

EXAMPLE 4

Preparation of δ-Natamycin 10 g of purified α-natamycin was suspended in 100 ml of methanol and stirred at room temperature. After 15 minutes the transformation of the α-natamycin into the methanol solvate was completed as could be detected under the microscope by the complete transformation of the platelets into needles. After stirring for 2 hours the crystals were filtered off and washed with 100 ml of methanol. By drying the crystalline mass for 20 hours in vacuo over $P_2O_5$ at room temperature the methanol was completely removed and 8.83 g of δ-natamycin was obtained. DSC analysis showed an endotherm at $T_{top}$ 126.7° C. (corresponding to 0.5 mole of water as indicated by TGA-analysis) and an endotherm immediately followed by an exotherm at respectively $T_{too}$ 182.4 and 186.8° C. (decomposition).

The crystallographic data of the obtained δ-natamycin are presented in table I.

The conversion of natamycin methanol solvate into δ-natamycin can also be established by heating the material at 52° C. in vacuo for 19 hours without using $P_2O_5$ or by subjecting the methanol solvate at room temperature for 72 hours to diminished pressure and a small continuous flow of nitrogen gas.

Stability of δ-Natamycin

Samples of 180 mg samples of δ-natamycin were stored at respectively 20° C., 4° C. and −35° C. in an air or in a nitrogen atmosphere. δ-Natamycin proved to be much more stable than the corresponding methanol solvate. As indicated by DSC δ-natamycin stored for 3 months at room temperature in an air atmosphere showed no trace of decomposition. Only a slight discoloration was observed.

EXAMPLE 5

Preparation of γ-Natamycin 10 g of purified α-natamycin was suspended in 100 ml of methanol. After stirring for 24 hours at room temperature the crystalline mass was filtered off and washed with 100 ml of methanol. After drying for 1 hour in vacuo at room temperature 9.98 g of natamycin methanol solvate was obtained. At ambient temperature the material was then subjected during 23 hours to vacuo of $P_2O_5$ to afford 8.84 g of δ-natamycin. Finally the δ-natamycin was exposed to an atmosphere of 76% relative humidity during three days yielding 9.67 g of γ-natamycin.

The DSC thermogram showed three endotherms at $T_{top}$ 42.8, 60.3 and 124.82 C. (water) and an endotherm immediately followed by an exotherm at $T_{too}$ 182.5 and 186.8° C. respectively (decomposition).

The crystallographic data of the γ-natamycin are presented in table I.

EXAMPLE 6

Preparation of α-Natamycin from the Methanol Solvate

At ambient temperature 1.0 g of natamycin methanol solvate was suspended in 100 ml of demineralized water.

The suspension was stirred for 25 hours. The crystals were filtered off and washed with respectively 25 ml of water and 50 ml of acetone and then dried overnight in a ventilation box at 35° C. 0.81 g of material was obtained of which the DSC thermogram was identical to α-natamycin. Typical data were: three endotherms at $T_{too}$ 44.6, 68.4 and 97.9° C. (water) and a small endotherm immediately followed by an exotherm at $T_{too}$ 216.2 and 230.0° C. respectively (decomposition).

EXAMPLE 7

Preparation of α-Natamycin from γ-Natamycin 1.0 g of γ-natamycin was suspended in 250 ml of demineralized water and the suspension stirred for 7 days at room temperature. The crystals were filtered off and washed with respectively 20 ml of water and 20 ml of acetone and then dried in a ventilation box at 30° C. to afford 0.92 g α-natamycin. This was confirmed by DSC analysis: endotherms at $T_{too}$ 45.2, 67.8 and 100.3° C. (water) and an endotherm immediately followed by an exotherm at $T_{top}$ 214.3 and 226.9° C. respectively (decomposition).

EXAMPLE 8

Preparation of α-Natamycin from δ-Natamycin 1.0 g of δ-natamycin was suspended in 100 ml of demineralized water and stirred for 24 hours. The crystals were collected by filtration, washed with respectively 25 ml of water and 50 ml of acetone and dried in a ventilation box at 35° C. to afford 1.02 g of α-natamycin. This was confirmed by DSC analysis: endotherms at $T_{too}$ 43.3, 67.8 and 100.3° C. (water) and an endotherm immediately followed by an exotherm at $T_{top}$ 215.0 and 226.8° C. respectively (decomposition).

EXAMPLE 9

Preparation of δ-Natamycin from γ-Natamycin 1.0 g of γ-natamycin was dried for 24 hours in vacuo over $P_2O_5$ affording 0.9 g of δ-natamycin, which was confirmed by DSC analysis: endotherm at $T_{too}$ 125.4° C. (water) and an endotherm immediately followed by an exotherm at $T_{top}$ 182.4 and 186.8° C. respectively (decomposition).

EXAMPLE 10

Preparation of the Calcium Salt of Natamycin

During 30 minutes a stream of nitrogen gas was passed through 150 ml of a filtered saturated solution of calcium hydroxide in demineralized water. Subsequently 3.0 g of α-natamycin was added and the mixture was stirred overnight at room temperature. The crystals were filtered off and washed with respectively 150 ml of demineralized water and 50 ml of acetone. The crystalline material was dried in a ventilation box at 35° C. to afford 2.34 g of calcium dinatamycinate as was confirmed by NMR analysis. The calcium content was 2.93%, which corresponded to 0.5 mole of Ca per mole of natamycin.

DSC data are: endotherms at $T_{too}$ 89.7 and 128.5° C. (the latter represents a loss of water of 2.07%, at a total water loss of 6.74% according to TGA analysis) and a very small endotherm immediately followed by an exotherm (decomposition) at $T_{top}$ 179.3 and 194.9° C. respectively. The crystallographic data of the obtained calcium salt of natamycin are presented in table I.

EXAMPLE 11

Preparation of the Barium Salt of Natamycin 32 g of barium hydroxide was dissolved in 800 ml of methanol. Nitrogen gas was passed through the solution. The turbid solution was then filtered and stored under nitrogen. While a stream of nitrogen gas was passed through the solution 5.0 g of purified α-natamycin was dissolved in 100 ml of the clarified barium hydroxide solution. Subsequently 250 ml of gas-free, demineralized water was slowly added. After the addition of 40 ml of water a precipitate was formed. After 30 minutes the crystals were filtered off and washed with 200 ml of a 1:1 (v/v) mixture of methanol and water. The product was dried in a ventilation box at 35° C. to afford 3.76 g of the barium salt of natamycin. According to elementary analysis the barium content of the obtained material was 8.14% corresponding to the formula of barium dinatamycinate.

The DSC thermogram showed an endotherm at $T_{too}$ 94.2° C. and a decomposition exotherm starting at 172.6° C. and with $T_{too}$ at 194.5° C. TG/DTA analysis detected a water-content of 6.58%.

The crystallographic data of the obtained barium salt of natamycin (consisting of rectangular plates) are presented in table I.

EXAMPLE 12

Preparation of Natamycin Methanol Solvate from δ-Natamycin 1.0 g of δ-natamycin, prepared from the corresponding methanol solvate by drying in vacuo at 52° C. for 19 hours, was stored in a desiccator and exposed to methanol vapour for 113 hours to yield 1.12 g of natamycin methanol solvate as indicated by DSC analysis: endotherms at $T_{top}$ 55.9 and 74.0° C. (methanol) and 124.8° C. (water) and an endotherm immediately followed by an exotherm (decomposition) at $T_{top}$ 181.1 and 186.1° C. respectively.

EXAMPLE 13

Preparation of Solvates of Natamycin from δ-Natamycin by the Action of the Vapour of Several Solvents on δ-Natamycin A 100 mg sample of δ-natamycin was put into a 8 ml vial. The open vial was then placed into a 125 ml flask containing a small layer of a solvent. Subsequently the flask was closed and stored at ambient temperature in the dark during 7 days. In this manner samples of δ-natamycin were subjected to the action of the vapour of several solvents. The solvates of natamycin with the following solvents were obtained:

Ethanol (6 mole)
1-propanol (2.5 mole)
1-butanol (1.5 mole)
2-methoxyethanol (2.5 mole)
ethyl formate (1 mole)
acetone (2 mole)
dichloromethane (1.3 mole)
acetonitrile (3 mole)
dimethylformamide (4.5 mole)

Between parentheses the amount of solvent (moles) per mole of natamycin is given as has been analyzed by NMR spectroscopy.

EXAMPLE 14

Preparation of Solvates of Natamycin from δ-Natamycin by Bringing the Natamycin into Contact with a Solvent In a 6 ml closed vial (snapcap) a 200 mg sample of δ-natamycin was stirred during 24 hours at 32° C. with 2 ml of a solvent. The crystalline material was then filtered off, washed with the applied solvent and dried on the filter under a stream of nitrogen gas until dry. Eventually the crystals were washed on the filter with a small portion of acetone of diethyl ether. Using this method the solvates of natamycin with the following solvents were obtained: methanol, ethanol, 1-propanol, 1-butanol, 2-methoxyethanol, methyl formate, acetonitrile, dimethyl sulphoxide, and formamide. The conversion of δ-natamycin to the solvates was confirmed by DSC analysis.

EXAMPLE 15

Preparation of Solvates of Natamycin from α-Natamycin by Bringing the Natamycin into Contact with a Solvent In a 6 ml closed vial (snapcap) a 200 mg sample of purified α-natamycin was stirred during 24 hours at 32° C. with 2 ml of a solvent. The crystalline material was then filtered off, washed with the applied solvent and dried on the filter under a steam of nitrogen gas until dry. Eventually the crystals were washed in the filter with a small portion of acetone of diethyl ether. Using this method the solvates of natamycin with the following solvents were obtained: methanol, ethanol and 2-methoxy ethanol. The conversions were confirmed by DSC analysis.

EXAMPLE 16

Preparation of Natamycin on Fumed Silca as the Carrier

A solution of 100 mg of α-natamycin in 25 ml of methanol was prepared. 1 ml of the solution was mixed with 200 mg of fumed silica (Aerosil® 200 V). Most of the methanol was evaporated by heating at 50° C. during 30 minutes at diminished pressure. Then another portion of 1 ml of the natamycin solution was added and after mixing the mass thoroughly most of the methanol was again removed by heating at 50° C. during 30 minutes at diminished pressure. The procedure was repeated until a total of 5 ml of the methanolic solution was added. Finally the mixture was dried overnight in a vacuum oven at about 50° C. and after grinding the resulting powder was stored under nitrogen gas in a closed bottle.

The release rate of the natamycin was determined using the method described in example 1. For this purpose 40 mg of the sample was suspended in 5 ml of water and 50 μl of the obtained suspension applied on the paper filter disc. Further the procedure of example 1 was followed. The result of the measurement is summarized in table II.

EXAMPLE 17

Release Rate of Several Natamycin Samples from Aqueous Suspensions

Using the method described in example 1 the release rate profile of several natamycin preparations were compared to each other.

Suspensions of the natamycin preparations were prepared, in such a manner that each suspension contained 800 ppm of the pure natamycin as such. 50 μl of each of the respective mixtures was applied on a paper filter disc and the release rate analyzed using the method of example 1. The results are summarized in table II.

The release rate of micronised natamycin is comparable to that of non micronised natamycin, while the modified natamycin types have a higher release rate during a longer time.

EXAMPLE 18

Release Rate of Several Natamycin Samples from Plasticoat®

Using the same method as described in example 18 also the release rate from Plasticoat® was measured. The concentration of the natamycin as such was in each case 800 ppm. 50 μg of each of the respective mixtures was applied on a paper filter disc and the release rate analyzed using the method of example 1. The results are summarized in Table III.

The release rate of micronised natamycin from Plasticoat® is comparable to that of non micronised natamycin, while the modified natamycin types have a higher release rate during a longer time.

EXAMPLE 19

Release Rate of Natamycin from Plasticoat®, With and Without Suspending the Natamycin in a Solvent System Prior to the Addition to the Plasticoat® Emulsion.

α-Natamycin was suspended in respectively water (1% w/v), methanol (1% w/v), glacial acetic acid (1% w/v), propylene glycol (1.5% w/v) and in ethanol which contain 20 g/l of ethanol amine (1% w/v). 1 part of each mixture was mixed with 19 parts of Plasticoat®, except for the solution in propylene glycol, which was mixed with 29 parts of Plasticoat®. 80 μl of the different Plasticoat® mixtures was applied on a paper filter disc and the release rate of the samples analyzed using the method described in example 1. The results are summarized in Table IV.

The release rate from the Plasticoat® emulsion prepared by prior dissolving the natamycin in a solvent system was higher than by first suspending the natamycin in water.

EXAMPLE 20

This example illustrates the effect towards Penicillium echinulatum var. discolor on cheese of natamycin compositions prepared according to the invention by dissolving the natamycin in methanol prior to the addition to the coating emulsion as compared to the effect of natamycin compositions prepared in conventional manner without prior dissolving of the antifungal compound.

For the experiment, five coating compositions were used.

Compositions A and B were compositions prepared according to the invention. The α-natamycin was first dissolved in methanol (1% w/v). This solution was then added to Plasticoat® (an aqueous emulsion of polyvinyl acetate supplied by National Starch & Chemical B.V.) in such a way that coating emulsions were obtained containing respectively 250 and 500 ppm of natamycin.

Compositions C and D were prepared by first making a suspension of α-natamycin in water (1% w/v) instead of a solution in methanol. This suspension was added to Plasticoat® in such a manner that coating emulsions were again obtained containing respectively 250 and 500 ppm of natamycin. Finally, a coating emulsion without natamycin was also used as a control (composition E).

The coating compositions were applied to the surface of pieces of Gouda cheese according to the following procedure:

A freshly brined wheel of Gouda cheese was first cut horizontally into two parts. Each part was then cut into pieces of 5 by 5 by 5 cm. Only pieces with a flat rind surface were taken for the experiment. The pieces of cheese were dipped into a bath of melted paraffin at 80° C. in such a manner that the rind surface remained free of paraffin, while the other five surfaces were covered by a thin film of solidified paraffin.

The rind surface was then inoculated with about $6 \times 10^3$ CFU/cm$^2$ of a mixture of spores of three strains of Penicillium echinulatum var. discolor (CBS numbers 611.92, 612.92 and 613.92). The inoculation was performed by applying 0.15 ml of a spore suspension containing about $10^6$ CFU/ml to the surface of the piece of cheese. The inoculum was evenly spread over the surface by means of a sterile swab, which was saturated with the spore suspension.

After standing overnight in closed plastic boxes at about 6° C., the pieces of cheese were treated with the different compositions. For each treatment, 5 pieces of cheese were taken. On each piece, 0.8 ml of the Plasticoat® composition was applied and evenly spread over the surface of the cheese by means of a sterile rectangular piece of plastic of about 2 by 5 cm. After standing for 2 hours at ambient conditions, the pieces of cheese were incubated at 15° C. and a relative humidity of 95%.

Every day the number of visible colonies formed on each piece of cheese was determined and the average number per piece calculated for each treatment. When the number of colonies on a piece of cheese exceeded the value of 30, the piece of cheese was considered to be totally covered with mould.

Figure 1:
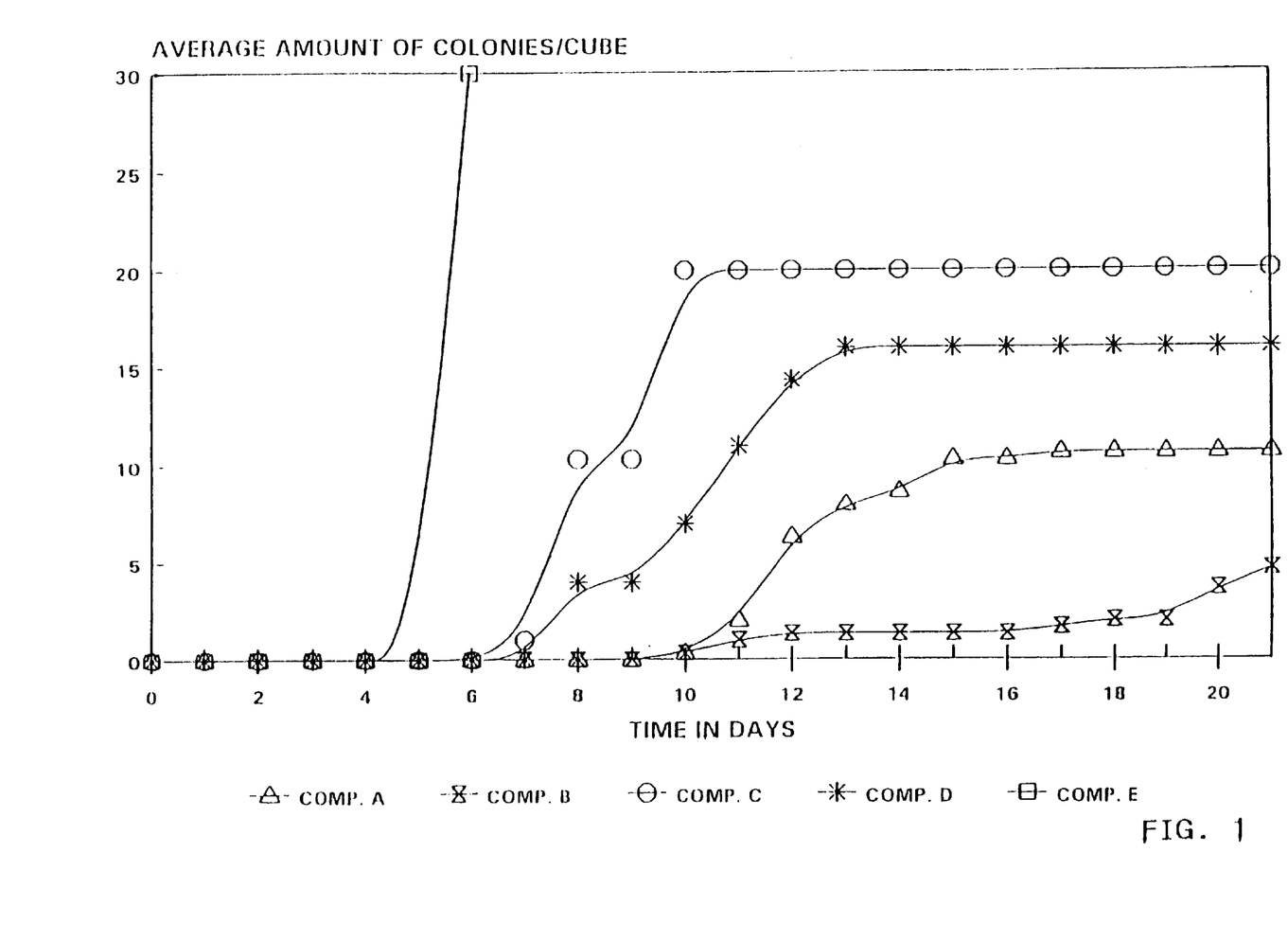
FIG. 1 (application of several compositions of natamycin on cheese) shows the mould inhibiting properties against *Penicillium echinulatum var. discolor* of several compositions containing 250 ppm and 500 ppm of natamycin compared to a blank composition (composition E). Composition C and composition D are references, while A and B are compositions according to the invention.

The results are summarised in FIG. 1.

The pieces treated with only Plasticoat® (control composition E) were totally covered with mould within 6 days. The pieces which were treated with the reference Plasticoat® compositions containing natamycin added as a suspension in water (compositions C and D) were free of mould for 6 and 8 days respectively, after which the average number of colonies gradually increased. After 11 to 12 days, the number of colonies reach 20 and 16 colonies respectively.

The pieces treated with the compositions according to the invention (A and B) were free of mould up to 10 days. The pieces treated with the composition containing 250 ppm of natamycin (A) reached a maximum average colony number of 11 colonies per cube after about 15 days of incubation. The average number of colonies formed on the pieces treated with composition B containing 500 ppm of natamycin remained below 5 for up to 21 days of incubation.

The results clearly demonstrate the superiority of the compositions according to the invention over the other tested compositions.

EXAMPLE 21

Figure 2:
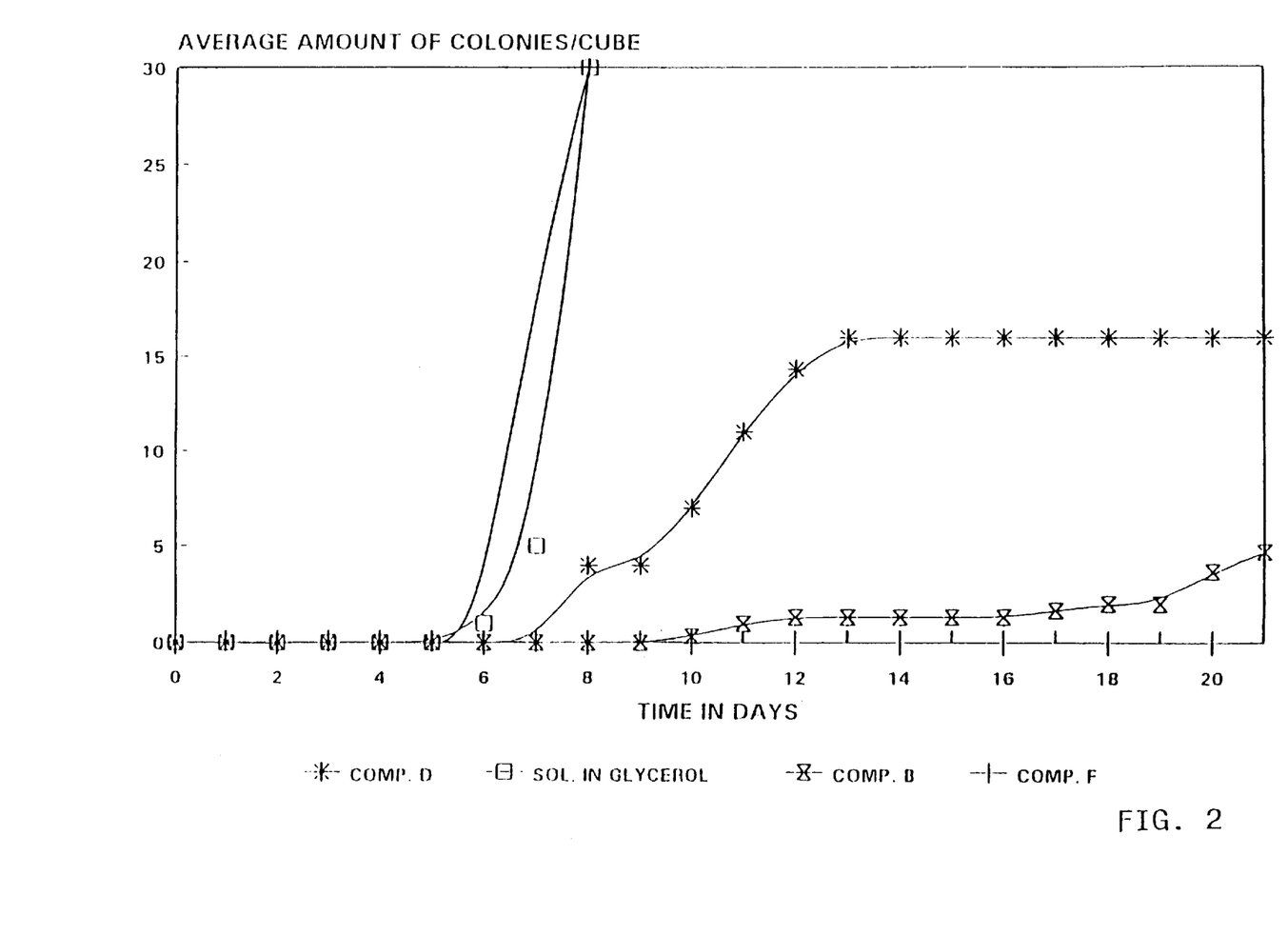
FIG. 2 (application of several compositions on cheese) shows the inhibiting effect against *Penicillium echinulatum var. discolor* of a solution of natamycin in glycerol as compared to a reference (composition D) and to a preparation according to the invention (composition B) and to a coating emulsion containing methanol only (composition F).

In the same experiment as described in Example 19 a solution of 500 ppm of α-natamycin in glycerol and a coating emulsion containing 5% (v/v) of methanol (composition F) were also used to treat cheese samples. FIG. 2 shows the results of these treatments as compared to a treatment with reference composition D and a treatment with a composition according to the invention (composition B). These results show that the treatment with dissolved natamycin was inferior even to treatment with the reference composition. Besides, the effect of the coating emulsion containing methanol in the same concentration as applied in composition D was also inferior to that of the reference composition.

EXAMPLE 22

Figure 3:
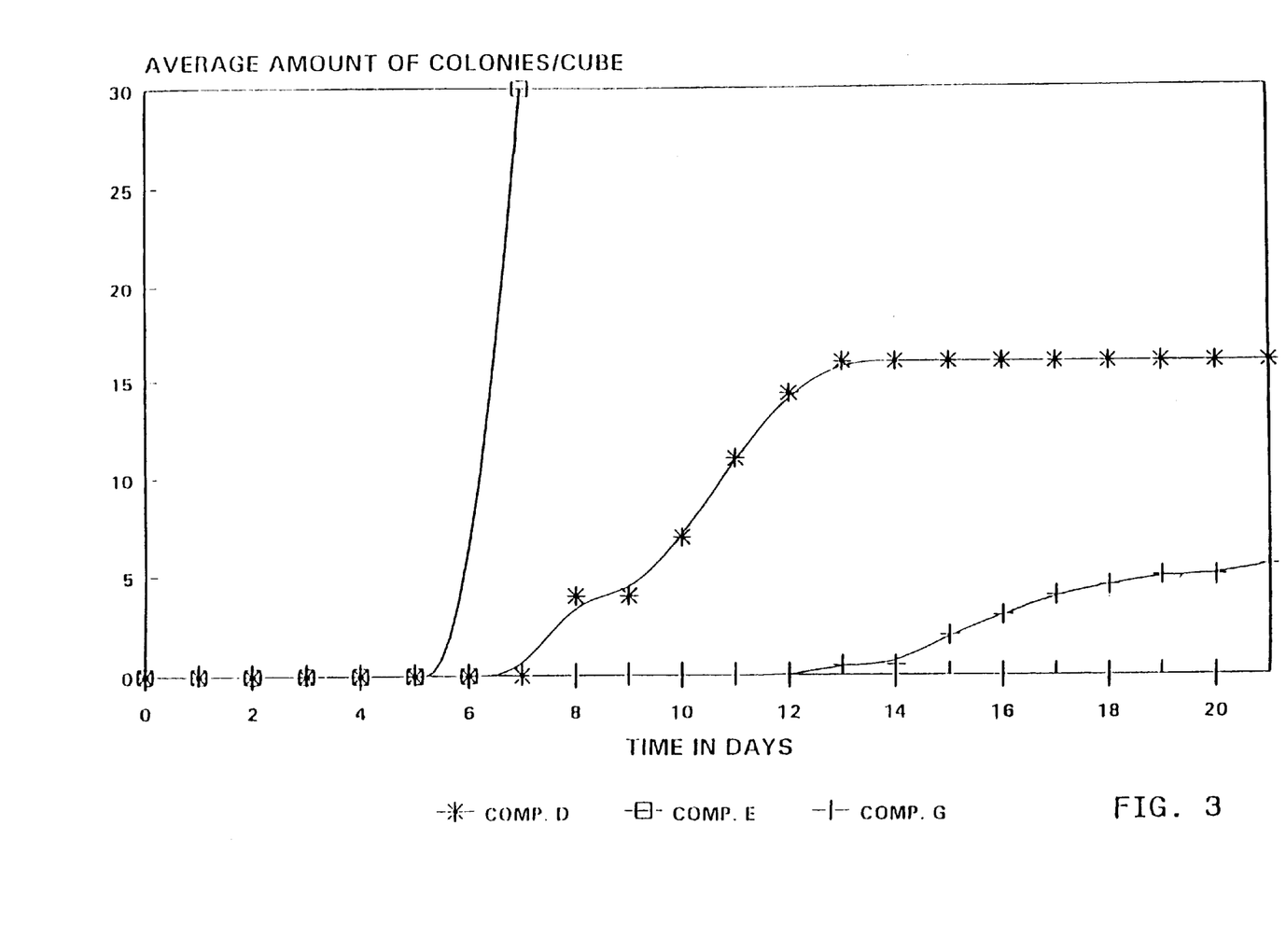
FIG. 3 (application of several natamycin preparations on cheese) shows the inhibiting effect against *Penicillium echinulatum var. discolor* of a coating emulsion containing natamycin which was added as a solution in glacial acetic acid to the coating (composition G) as compared to a reference (composition D) and to a blank coating emulsion (composition E).

In the same way as described in Example 19 an experiment was carried out using a Plasticoat® emulsion to treat the cheese samples containing 500 ppm of natamycin which was dissolved in glacial acetic acid (1% w/v) before adding the natamycin to the emulsion (composition G). As references Plasticoat® emulsions were used without natamycin (composition E) and containing 500 α-natamycin which was added as a 1% (w/v) emulsion in water to the coating composition (composition D). The results are given in FIG. 3 and demonstrate that the mould inhibiting properties towards Penicillium echinulatum var. discolor of the composition according to the invention (G) is better than those of the reference compositions D and E.

EXAMPLE 23

Pieces of Gouda cheese were prepared in the same way as described in Example 19 and the rind surfaces were then inoculated with about $6 \times 10^3$ CFU/cm$^2$ of a mixture of spores of three strains of Penicillium echinulatum var. discolor (CBS numbers 611.92, 612.92 and 613.92).

After standing overnight in closed plastic boxes at about 6° C., the pieces of cheese were treated with a blank Plasticoat® emulsion and Plasticoat® emulsions containing respectively 500 ppm of α-natamycin (composition D), 500 ppm of γ-natamycin (composition J) and 500 ppm of δ-natamycin (composition K). The natamycin preparations were suspended in water (1% w/v) prior to the addition to the Plasticoat®. For each treatment, 5 pieces of cheese were taken. On each piece, 0.8 ml of the Plasticoat composition was applied and evenly spread over the surface of the cheese by means of a sterile rectangular piece of plastic of about 2 by 5 cm. After standing for 2 hours at ambient conditions, the pieces of cheese were incubated at 15° C. and a relative humidity of 95%. The mould inhibiting effect was assessed in the same way as described in example 19.

Figure 4:
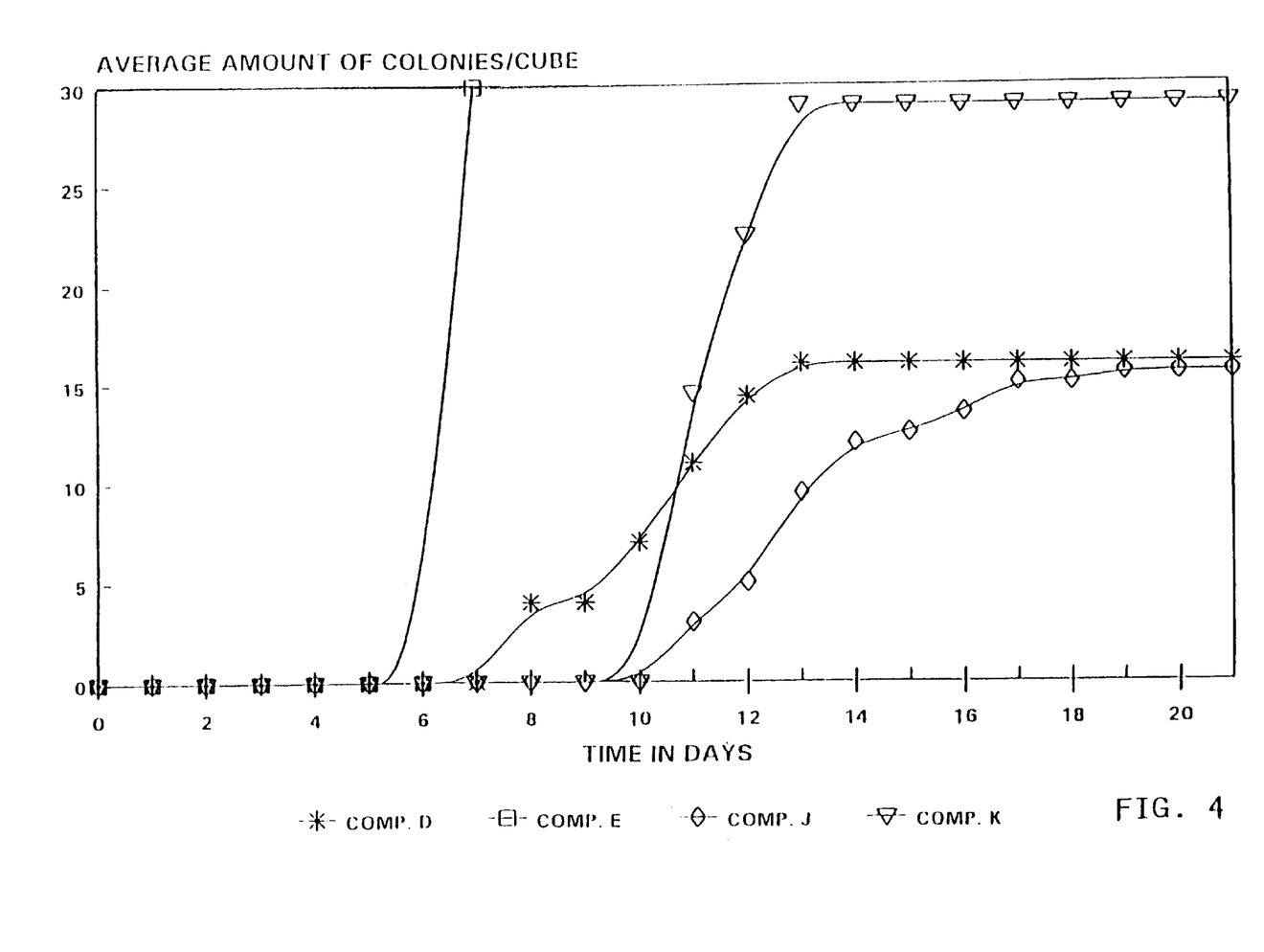
FIG. 4 (application of several natamycin preparations on cheese) shows the inhibiting effect against *Penicillium echinulatum var. discolor* of coating emulsions containing γ-natamycin (composition J) or δ-natamycin (composition K) as compared to a reference coating emulsion containing α-natamycin (composition D) and to a blank coating emulsion (composition E).

The results are given in FIG. 4. The pieces of cheese treated with composition J or K were free of mould during 10 days while the pieces treated with the reference was free of mould during only 7 days.

EXAMPLE 24

Pieces of Gouda cheese were prepared in the same way as described in Example 19 and the rind surfaces were then inoculated with about $6 \times 10^3$ CFU/cm$^2$ of a mixture of spores of three stains of Penicillium echinulatum var. discolor (CBS numbers 611.92, 612.92 and 613.92).

After standing overnight in closed plastic boxes at about 6° C., the pieces of cheese were treated with a blank Plasticoat® emulsion and Plasticoat® emulsions containing respectively 500 ppm of α-natamycin (composition D), 500 ppm of calcium dinatamycinate (composition L) and 500 ppm of barium dinatamycinate (composition M). The Plasticoat® emulsions containing the natamycin preparations were prepared by first suspending the natamycin preparations in water (1% w/v) and mixing the obtained suspensions with 19 parts of Plasticoat®. For each treatment, 5 pieces of cheese were taken. On each pieces, 0.3 ml of the Plasticoat® composition was applied and evenly spread over the surface of the cheese by means of a sterile rectangular piece of plastic of about 2 by 5 cm. After standing for 2 hours at ambient conditions, the pieces of cheese were incubated at 15° C. and a relative humidity of 95%. The mould inhibiting effect was assessed in the same way as described in example 19.

Figure 5:
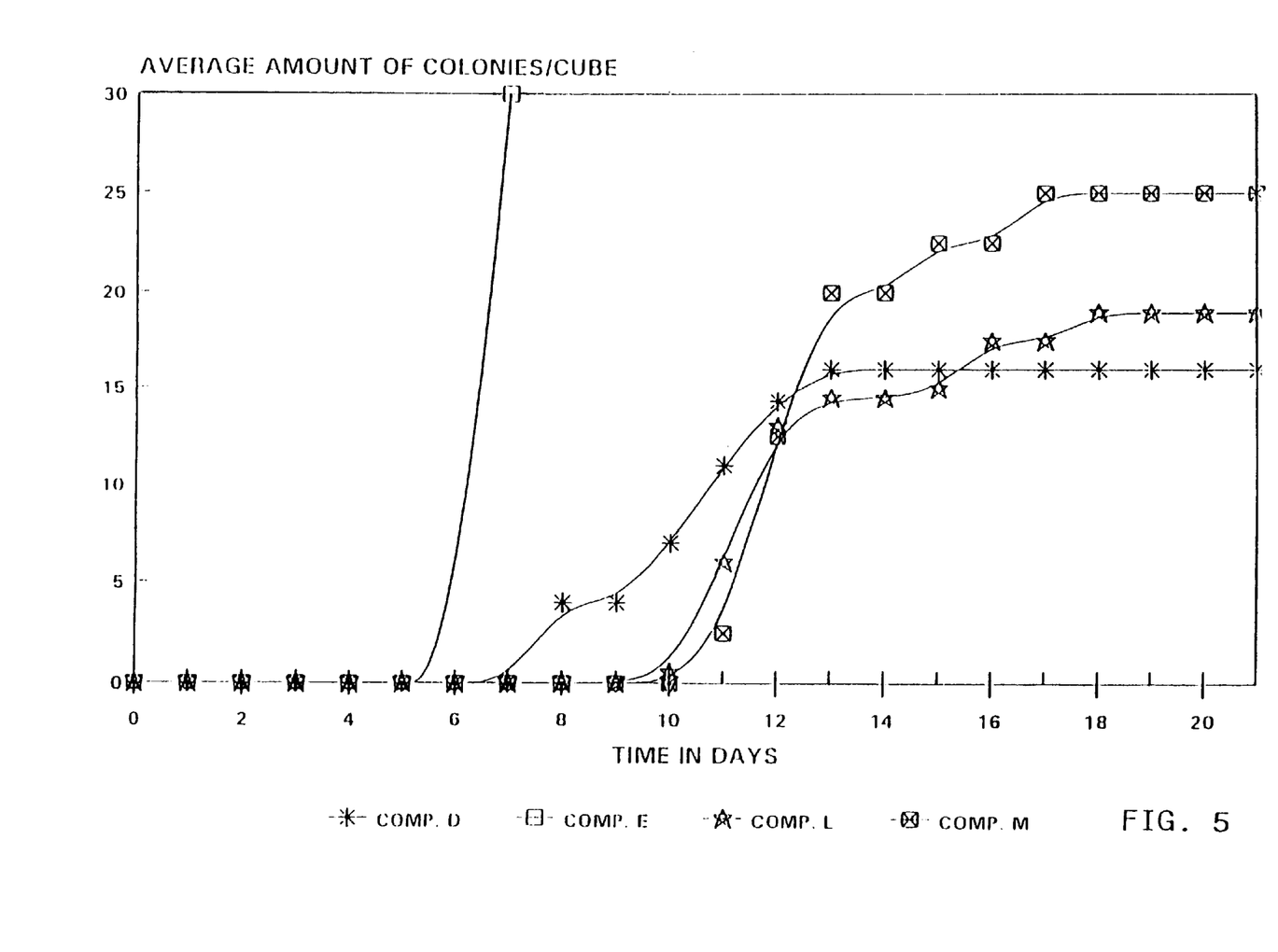
FIG. 5 (application of several natamycin preparations on cheese) shows the inhibiting effect against *Penicillium echinulatum var. discolor* of coating emulsions containing the calcium salt of natamycin (composition L) or the barium salt of natamycin (composition M) as compared to a reference coating emulsion containing α-natamycin (composition D) and to a blank coating emulsion (composition E).

The results are given in FIG. 5. The pieces treated with the calcium salt or with the barium salt (resp. composition L and composition M) were free of mould during 10 days and the reference pieces during only 7 days.

EXAMPLE 25

Pieces of Gouda cheese were prepared in the same way as described in Example 19 and the rind surfaces were then inoculated with about $1.2 \times 10^4$ CFU/cm$^2$ of spores of Aspergillus ochraceus (CBS numbers 659.93) by applying 0.15 ml of a spore suspension containing $2 \times 10^6$ CFU/ml to surface of the piece of cheese. After standing overnight in closed plastic boxes at about 6° C., the pieces of cheese were treated with three different Plasticoat® emulsions; a blank Plasticoat® emulsion, a Plasticoat® emulsion containing 500 ppm of α-natamycin which was suspended in water (1% w/v) before mixing with the emulsion and a Plasticoat® emulsion containing 500 ppm of natamycin which was dissolved in glacial acetic acid (1% w/v) prior to the addition to the Plasticoat®. For each treatment, 5 pieces of cheese were taken. On each piece, 0.8 ml of the Plasticoat® composition was applied and evenly spread over the surface of the cheese by means of a sterile rectangular piece of plastic of about 2 by 2 cm. After standing for 2 hours at ambient conditions, the pieces of cheese were incubated at 15° C. and a relative humidity of 95%.

Every day the amount of visible colonies formed on the pieces of cheese was counted and the average amount per piece calculated. When the amount of colonies on a piece of cheese exceeded the value of 50, the piece of cheese was considered to be totally covered with mould.

Figure 6:
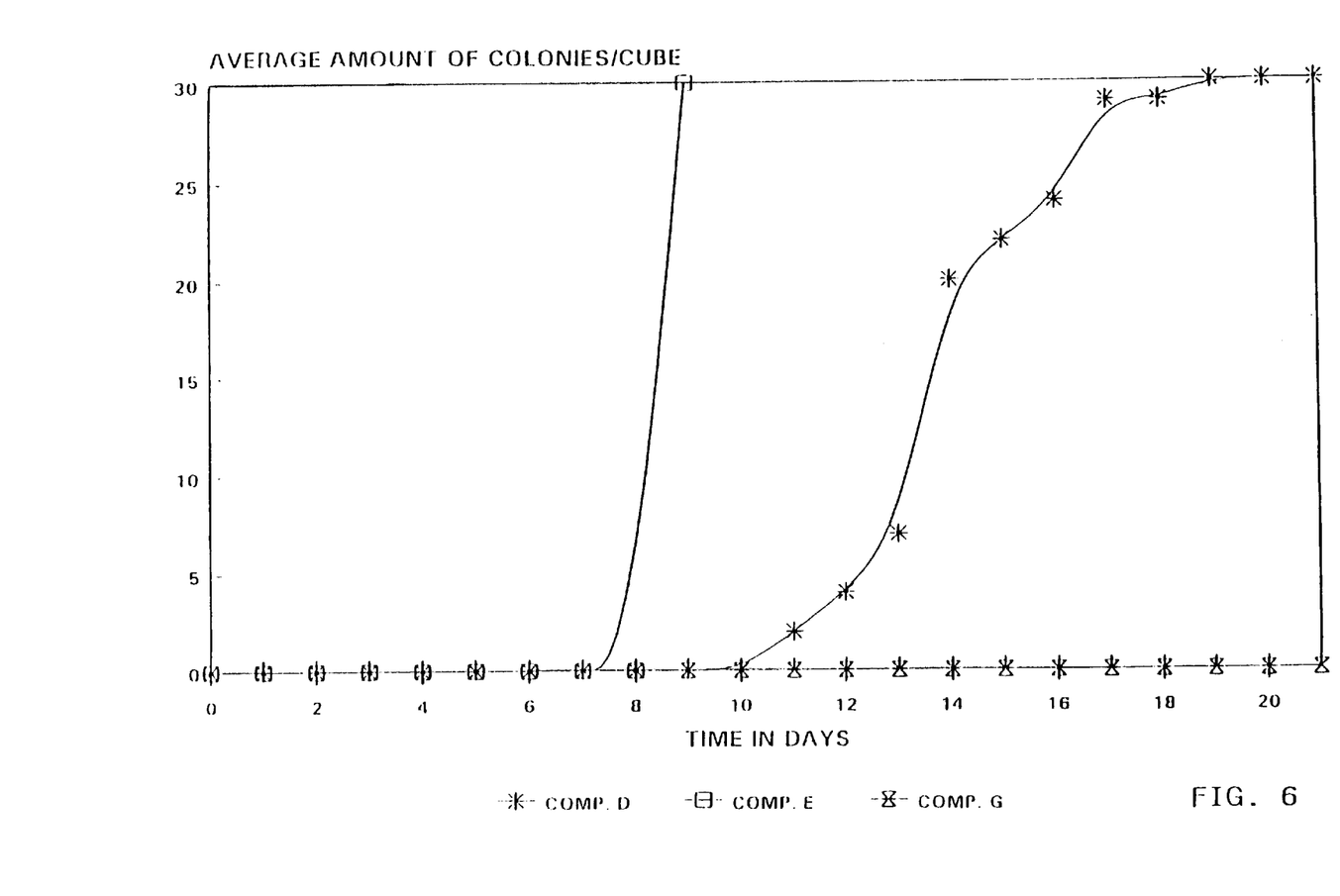
FIG. 6 (application of several natamycin preparations on cheese) shows the inhibiting effect against *Aspergillus ochracheus* of a coating emulsions containing natamycin which was added as a solution in glacial acetic acid to the coating (composition G) as compared to a reference (composition D) and to a blank coating emulsion (composition E).

The results are summarized in FIG. 6.

It is clear that the treatment with a composition according to the invention (composition G) results in a protection against growth of Aspergillus ochraceus which was much better than a treatment with the blank (composition ) or with natamycin which was added to the coating emulsion via an aqueous suspension (composition D).

TABLE II

Release rate of different types of natamycin suspended in water as analyzed according to the method described in example 1. (Each paper filter disc was loaded with 40 µg of natamycin)

| Natamycin Type | Amount of days that the dissolution is higher than: | | | | | |
|---|---|---|---|---|---|---|
| | 0 µg | 1 µg | 2 µg | 3 µg | 4 µg | 5 µg |
| α-Natamycin (not micronised) | >5 | >5 | 2 | 0 | 0 | 0 |
| α-Natamycin (micronised) | >5 | >5 | 3 | 0 | 0 | 0 |
| γ-Natamycin | >5 | >5 | >5 | 3 | 1 | 0 |
| δ-Natamycin | >5 | >5 | >5 | 3 | 1 | 0 |
| Calcium dinatamycinate | >5 | >5 | >5 | >5 | 4 | 2 |
| Barium dinatamycinate | >5 | >5 | >5 | >5 | 3 | 3 |
| Natamycin methanol solvate | >5 | >5 | >5 | >5 | >5 | >5 |
| Natamycin ethanol solvate | >5 | >5 | >5 | >5 | >5 | >5 |
| Natamycin 1-butanol solvate | >5 | >5 | >5 | 3 | 1 | 0 |
| Natamycin acetone solvate | >5 | >5 | >5 | >5 | >5 | >5 |
| Natamycin dichloromethane solvate | >5 | >5 | >5 | 3 | 1 | 0 |
| Natamycin on fumed silica | >5 | >5 | >5 | 2 | 1 | 0 |

TABLE III

Release rate of different natamycin preparations from Plasticoat ® as analyzed according to the method described in example 1. (Loading concentration 40 µg per filter paper disc)

| Natamycin Type | Amount of days that the dissolution is higher than: | | | | | |
|---|---|---|---|---|---|---|
| | 0 µg | 1 µg | 2 µg | 3 µg | 4 µg | 5 µg |
| α-Natamycin (non micronised) | >5 | >5 | 0 | 0 | 0 | 0 |
| α-Natamycin (micronised) | >5 | >5 | 1 | 0 | 0 | 0 |
| γ-Natamycin | >5 | >5 | 3 | 1 | 0 | 0 |
| δ-Natamycin | >5 | >5 | 3 | 1 | 0 | 0 |

TABLE I

Crystallographic data of different natamycin preparations as derived from the X-ray pattern determinations. The X-ray diagrams were determined by utilizing Cukα radiation and a Guinier camera with a Johansson type monochromator.

| | α-Natamycin | γ-Natamycin | δ-Natamycin | Natamycin methanol-solvate | Calcium dinata-mycinate | Barium dinata-mycinate |
|---|---|---|---|---|---|---|
| Crystal Structure | Monoclinic | Orthorhombic | Orthorhombic | Orthorhombic | Triclinic | Monoclinic |
| Space Group | P2$_1$ | Pnam | Pmnm | P2$_1$2$_1$2$_1$ | PI | P2$_1$ |
| Cell Dimensions[1] | a = 8.70 Å<br>b = 26.78 Å<br>c = 7.65 Å<br>α = 92.44* | a = 16.78 Å<br>b = 29.25 Å<br>c = 7.95 Å | a = 16.96 Å<br>b = 26.22 Å<br>c = 14.14 Å | a = 18.97 Å<br>b = 23.78 Å<br>c = 8.64 Å | a = 16.78 Å<br>b = 28.37 Å<br>c = 7.59 Å<br>α = 93.75*<br>β = 90.01*<br>γ = 98.53 | a = 8.95 Å<br>b = 55.35 Å<br>c = 14.96 Å<br>α = 92.28* |
| Unit Cell Volume | 1782 Å$^3$ | 3903 Å$^3$ | 6765 Å$^3$ | 3896 Å$^3$ | 3564 Å$^3$ | 7401 Å$^3$ |
| Volume per Formula Unit | 891 Å$^3$ | 967 Å$^3$ | 846 Å$^3$ | 974 Å$^3$ | 891 Å$^3$ | 925 Å$^3$ |
| Z[2] | 2 | 4 | 8 | 4 | 4 | 8 |

[1] To make comparisons between the different elementary cells possible the a- and the b- axis of the elementary cells of α-natamycin and of the barium salt have been switched with each other.
[2] Formula units per unit cell

TABLE III-continued

Release rate of different natamycin preparations from Plasticoat ® as analyzed according to the method described in example 1.
(Loading concentration 40 μg per filter paper disc)

| Natamycin Type | Amount of days that the dissolution is higher than: | | | | | |
|---|---|---|---|---|---|---|
| | 0 μg | 1 μg | 2 μg | 3 μg | 4 μg | 5 μg |
| Calcium dinatamycinate | >5 | >5 | 3 | 0 | 0 | 0 |
| Barium dinatamycinate | >5 | >5 | 3 | 0 | 0 | 0 |
| Natamycin methanol solvate | >5 | >5 | 3 | 1 | 0 | 0 |
| Natamycin ethanol solvate | >5 | 3 | 2 | 1 | 0 | 0 |
| Natamycin 1-butanol solvate | >5 | >5 | 3 | 0 | 0 | 0 |
| Natamycin acetone solvate | >5 | >5 | 3 | 2 | 0 | 0 |
| Natamycin dichloromethane solvate | >5 | >5 | 3 | 1 | 0 | 0 |

TABLE IV

Release rate of different natamycin samples from Plasticoat ® as analyzed according to the method described in example 1. The (α-)natamycin was dissolved in a solvent prior to the addition to the Plasticoat ®. (Final concentration in the Plasticoat ® 500 ppm and loading concentration 40 μg per filter paper disc)

| Solvent system (concentration of natamycin in the system) | Amount of days that the dissolution is higher than: | | | | | |
|---|---|---|---|---|---|---|
| | 0 μg | 1 μg | 2 μg | 3 μg | 4 μg | 5 μg |
| Water (1% w/v) | >5 | >5 | 0 | 0 | 0 | 0 |
| Methanol (1% w/v) | >5 | >5 | >5 | 1 | 0 | 0 |
| Glacial acetic acid (1% w/v) | >5 | >5 | 5 | 4 | 3 | 3 |
| Propylene glycol (1.5% w/v) | >5 | >5 | 5 | 1 | 0 | 0 |
| Ethanol + ethanol amine (1% w/v)*) | >5 | >5 | >5 | 0 | 0 | 0 |

*)The concentration of the ethanolamine was 2% (w/v)

REFERENCES

1. Jedrychowski, L.; Reps, A.; Jarmul, I.; Babuchowski, A. "Use of natamycin for a protection of semihard cheese against moulding" Brief communications of the XXIII International Dairy Congress, Montreal, Oct. 8–12, 1990, Vol. I.
2. Daamen, C. B. G. and Berg, G. van den; "Prevention of mould growth on cheese by means of natamycin" Voedingsmiddelentechnologie, 18 (2), 26–29, (1985)
3. Neviani, E.; Emaldi, G. C.; Carini, S,; "Use of pimaricin as a fungicide on cheese rind: technology and the effects on the cheese surface flora" Latte, 6 (5), 335–343, (1981)
4. Morris, H. A.; Castberg, H. B.; "Control of surface growth on Blue cheese using pimaricin" Cultured Diary Products Journal, 15 (2), 21–23, (1980)
5. Baldini, P.; Palmia, F.; Raczynski, R. G.; Campanini, M.; "Use of pimaricin for preventing mould growth on Italian cured meat products" Indutria Conserve, 54 (4), 305–307, (1979)
6. Weiss, G.; "Preservation of dairy products with chemicals" Deutsche Molkerei Zeitung 91 (50), 2351–2356, (1970)
7. Holley, R. A.; "Effect of sorbate and pimaricin on surface mould and ripening of Italian dry salami" Lebensmittel Wissenschaft und Technolgie 19 (1), 59–65, (1986).
8. Ruig, W. G.; Berg, G. van den; "Influence of the fungicides sorbate and natamycin in cheese coatings on the quality of the cheese" Netherlands Milk and Dairy Journal, 39 (3), 165–172, (1985)
9. Holley, R. A.; "Prevention of surface mould growth on Italian dry sausage by natamycin and potassium sorbate" Applied and Environmental Microbiology, 41 (2), 422–429, (1981)
10. Lueck, H.; Cheesman, C. E.; "Mould growth on cheese as influenced by pimaricin (natamycin) or sorbate treatments" South African Journal of Dairy Technology, 10 (3), 143–146, (1978)
11. Mattson, N.; "Mould control on cheese. Experience with potassium sorbate (added to brine) and pimaricin for surface treatment of hard cheese" Svenska Mejeritidningen 69 (3), 14–15, (1977)
12. Verma, H. S.; Yadav, J. S.; Neelakantan, S.; "Preservative effect of selected antifungal agents on butter and cheese" Asian Journal of Dairy Research 7 (1), 34–38, (1988)
13. Clark, W. L.; Shirk, R. J.; Kline E. F.; "Pimaricin, anew food fungistat" Microbial Inhibitors in Food, Edition N. Molin, 167–184, (1964)
14. Brik, H.; "Natamcyin" Analytical Profiles of Drug Substances 10, 513–561, (1981)
15. Ghielmetti, G.; Bruzzese, T.; Bianchi, C.; Recusani, F.; "Relationship between Acute Toxicity in Mice and Polymorphic Forms of Polyene Antibiotics" Journal of Pharmaceutical Sciences 65 (6), 905–907, (1976)

What is claimed is:

1. A natamycin solvate crystal that comprises natamycin and a solvent, wherein said natamycin and solvent are present in a specified molar ratio in the crystal thereof, and wherein said solvate, and molar ratio therein, are selected from the group consisting of:
   (a) natamycin:ethanol (1:6);
   (b) natamycin:1-propanol (1:2.5);
   (c) natamycin:ethyl formate (1:1);
   (d) natamycin:acetone (1:2);
   (e) natamyin:dichloromethane (1:1.3);
   (f) natamycin:acetonitrile (1:3); and
   (g) natamycin:dimethylformamide (1:4.5).

2. An antifungal composition suitable for topical application prepared by the method of:
   (a) contacting a polyene type antifungal compound selected from the group consisting of natamycin, lucensomycin, nystatin and amphotericin B with a substantially non-aqueous solvent, so as to convert said antifungal compound into a solvated form;
   (b) removing said solvent from said solvated antifungal compound under anhydrous conditions;
   (c) contacting said antifungal compound of step (b) with a humid environment;
   (d) recovering said antifungal compound as a hydrated form which form has enhanced activity towards fungal species with a low susceptibility to untreated natamycin; and
   (e) adding a pharmaceutical excipient to the hydrated compound recovered in step (d).

3. An antifungal composition suitable for topical application prepared by the method of:
   (a) contacting a polyene type antifungal compound selected from the group consisting of natamycin, lucensomycin, nystatin and amphotericin B with a substantially non-aqueous solvent, so as to convert said antifungal compound into a solvated form;
   (b) removing said solvent from said solvated antifungal compound under anhydrous conditions;
   (c) recovering said antifungal compound in anhydrous form which form has enhanced activity towards fungal species with a low susceptibility to untreated natamycin; and (d) adding a pharmaceutical excipient to the anhydrous compound recovered in step (c).

4. An isolated solid form-alkaline earth salt of polyene type antifungal compound having enhanced dissolution in water and activity towards fungal species with a low susceptibility relative to sodium salts of natamycin selected from the group consisting of natamycin, lucensomycin, nystatin and amphotericin B, wherein the alkaline earth salt is selected from the group consisting of calcium and barium salts.

5. An antifungal composition according to claim 2 wherein solvent is removed in step (b) of the preparation thereof by a method selected from the group consisting of:

subjecting said solvated antifungal compound to diminished pressure;

heating said solvated antifungal compound under diminished pressure;

subjecting said solvated antifungal compound to a stream of inert gas; and     subjecting said solvated antifungal compound to diminished pressure over a drying agent.

6. An antifungal composition according to claim 3 wherein solvent is removed in step (b) of the preparation thereof by a method selected from the group consisting of:

subjecting said solvated antifungal compound to diminished pressure;

heating said solvated antifungal compound under diminished pressure;

subjecting said solvated antifungal compound to a stream of inert gas; and     subjecting said solvated antifungal compound to diminished pressure over a drying agent.

7. The natamycin solvate crystal of claim 1, wherein the solvate is stable under refrigeration and/or inert atmosphere conditions for three months or more.

\* \* \* \* \*